United States Patent [19]

Itoh

[11] Patent Number: 5,224,477
[45] Date of Patent: Jul. 6, 1993

[54] CURRENT-ASSISTED NERVE CELL CONNECTION

[75] Inventor: Hiroyasu Itoh, Shizuoka, Japan

[73] Assignee: Hamamatsu Photonics K.K., Shizuoka, Japan

[21] Appl. No.: 782,952

[22] Filed: Oct. 25, 1991

[30] Foreign Application Priority Data

Oct. 26, 1990 [JP] Japan .................................. 2-289401

[51] Int. Cl.⁵ .................................................. A61N 1/00
[52] U.S. Cl. .................................. 128/419 R; 128/421; 128/784
[58] Field of Search ............ 128/419 R, 419 C, 420 R, 128/420.5, 420.6, 421, 422, 783, 784

[56] References Cited

U.S. PATENT DOCUMENTS

| | | | |
|---|---|---|---|
| 3,858,586 | 1/1975 | Lessen | 128/4 |
| 4,011,872 | 3/1977 | Komiya | 128/321 |
| 4,561,851 | 12/1985 | Ferreira et al. | 128/421 |
| 4,632,116 | 12/1986 | Rosen et al. | 128/419 R |
| 4,867,164 | 9/1989 | Zabara | 128/421 |
| 4,892,105 | 1/1990 | Prass | 128/741 |
| 4,919,140 | 4/1990 | Borgens et al. | 128/422 |
| 4,934,368 | 6/1990 | Lynch | 128/420.6 |
| 4,955,378 | 9/1990 | Grasso | 128/421 |

FOREIGN PATENT DOCUMENTS

3041478A1 6/1982 Fed. Rep. of Germany .
3042437A1 6/1982 Fed. Rep. of Germany .

Primary Examiner—William E. Kamm
Assistant Examiner—George Manuel
Attorney, Agent, or Firm—Finnegan, Henderson, Farabow, Garrett & Dunner

[57] ABSTRACT

Ends of a pair of electrodes are positioned near the nerve cells to be connected while the portion under operation of a living body is being observed with a TV monitor. By applying a DC micro-current or high voltage pulse current to the living body via the pair of electrodes, the nerve cells are connected. The connection is confirmed by applying electric stimulation to the living body between a stimulating electrode and a monitor electrode, and monitoring its reaction on an oscilloscope. Each of the pair of electrodes has a needle-like electrode member which is shielded by an insulating cover member such that only a part thereof is exposed, and that the exposed parts of the electrodes are opposed to each other.

17 Claims, 8 Drawing Sheets

SECRETION OF NGFs 101    102

FIG. 8(b) PRIOR ART

103  EXTENSION OF AXIS CYLINDER 101    102

CURRENT-ASSISTED NERVE CELL CONNECTION

BACKGROUND OF THE INVENTION

The present invention relates to a technique of connecting nerve cells in a living body to each other.

The nerve growth mechanism has not been made clear. However, there have been reported some investigation results on external and internal factors. As an example of the external factor, the NGF (nerve growth factor) for sensory nerves contained in a mouse tumor is known.

Figure 8A:
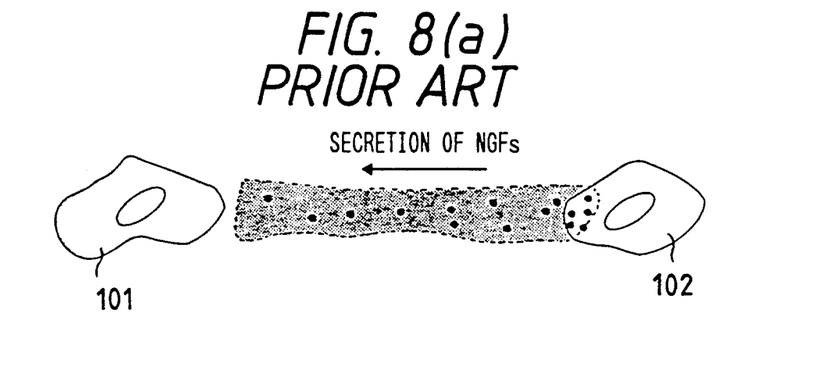
FIGS. 8(a)-8(c) are diagrams showing a nerve growth mechanism.
Figure 8B:
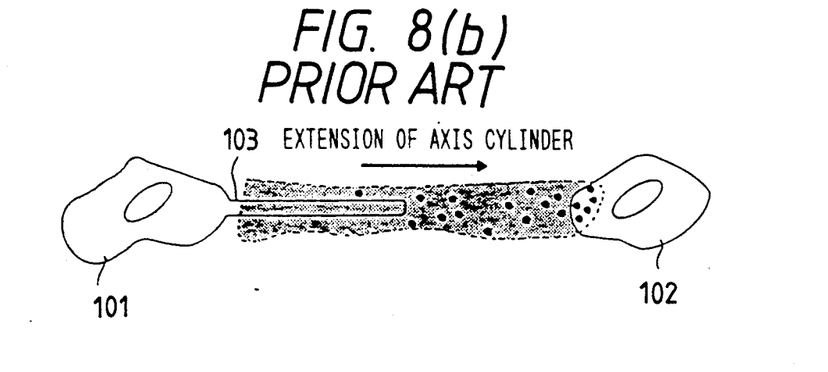
Figure 8C:
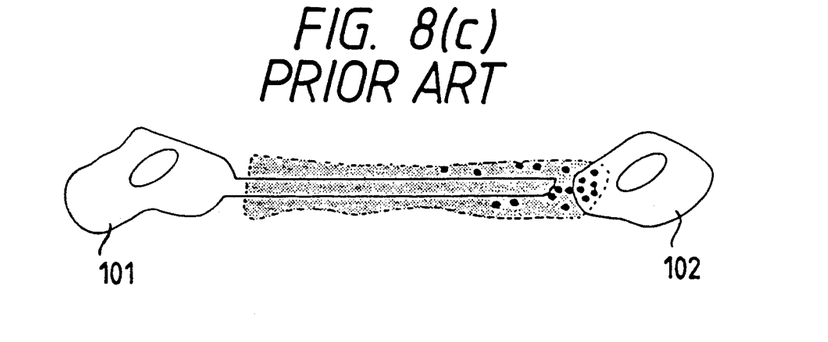

This will be explained with reference to FIGS. 8(a)-8(c). If a target cell 102 exists in the vicinity of a neuron 101 of a sympathetic ganglion, NGFs are secreted from the target cell 102 (FIG. 8(a)). Then, an axis cylinder 103 extends from the neuron 101 (FIG. 8(b)) and finally reaches the target cell 102, so that the neuron 101 is connected to the target cell 102 (FIG. 8(c)).

Figure 9A:
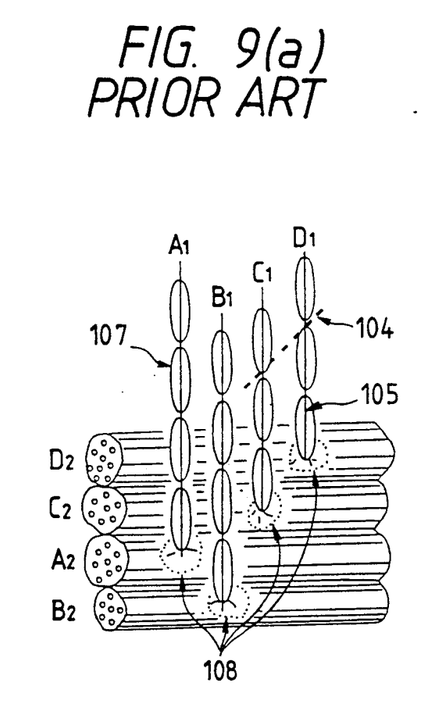
FIGS. 9(a) and 9(b) are diagrams showing how synapse connection of nerve cells occurs through germination of an axis cylinder.
Figure 9B:
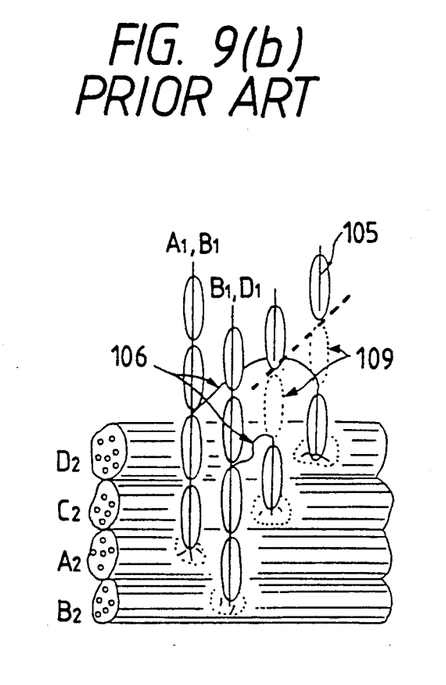

The mechanism in which a lateral branch germinates and extends from an axis cylinder of a nerve cell to create synapse connection of nerves is explained, for example, as illustrated in FIGS. 9(a) and 9(b). Assume that nerve cells $A_1$-$D_1$ are connected to muscle fibers $A_2$-$D_2$ respectively as shown in FIG. 9(a). If the nerve cells $C_1$ and $D_1$ are cut off along broken line 104 for some reason, the muscle fibers $C_2$ and $D_2$ can not react to stimulation any more. After a lapse of time, however, lateral branches 106 germinate from axis cylinders 105 of the nerve cells $C_1$ and $D_1$, and gradually extend. The branches 106 are finally connected to other nerve cells in about two weeks. In FIG. 9(a), reference numeral 107 and 108 represent a Schwann cell and a nerve ending. In FIG. 9(b), numeral 109 denotes a degenerated cell.

However, two weeks, which nerve cells take to connect to each other on a natural mechanism, are too long and cause inconveniences for the purposes of experiments or medical treatments. Consequently, it is desired to realize faster connection of nerve cells.

SUMMARY OF THE INVENTION

An object of the present invention is therefore to provide a technique of connecting nerve cells more easily in a positive manner.

The present invention is based on the inventor's consideration that connection of nerve cells may be facilitated by causing a DC micro-current or a pulse current to flow between the nerve cells to be connected.

According to the invention, an apparatus for connecting nerve cells of a living body comprises:

a pair of electrodes arranged substantially in parallel with each other with an interval which is suitable for placing the pair of electrodes near the nerve cells to be connected;

manipulating means for adjusting a position of the pair of electrodes;

observing means for magnifying an image of a portion under operation of the living body, and for displaying the magnified image; and power source means for applying a voltage across the pair of electrodes.

Further, according to the invention, an electrode unit for use in connecting tissues of a living body comprises:

a body casing; and a pair of electrodes attached to the body casing so as to be substantially parallel with each other, each of the pair of electrodes comprising:

a needle-like electrode member;

an insulating cover member for covering the needle-like electrode member; and conducting portion formed in the insulating cover member at a distal position of the electrode, for enabling current conduction to the needle-like electrode member, the conducting portions of the pair of electrodes being arranged so as to face each other.

DESCRIPTION OF THE PREFERRED EMBODIMENTS

Referring to the accompanying drawings, embodiments of the present invention will be described hereinafter.

Figure 1:
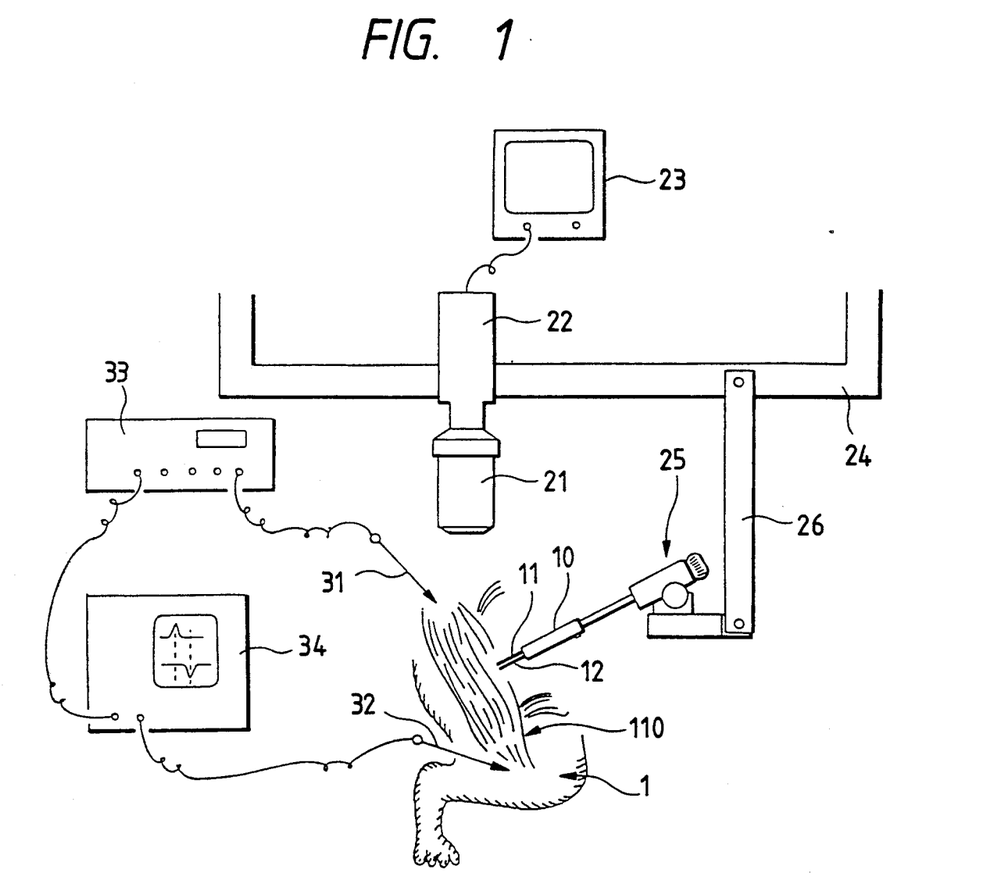
FIG. 1 is a schematic diagram showing the construction of a nerve-cell connecting apparatus according to an embodiment of the present invention.

FIG. 1 shows the whole construction of a nerve-cell connecting apparatus according to the present invention, and FIGS. 2(a)-2(c) and 3(a)-3(b) show the structure of electrodes to be used in the apparatus of FIG. 1.

In order to facilitate the understanding of the apparatus according to the invention, a cell connecting technique underlying the apparatus of FIG. 1 will be described first with reference to FIGS. 4(a) and 4(b).

Figure 4A:
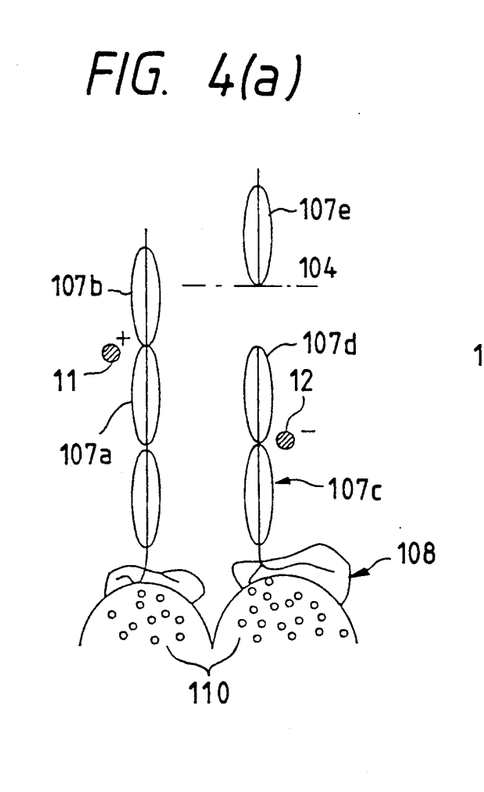
FIGS. 4(a) and 4(b) are diagrams schematically showing how nerve cells are connected with the aid of a micro-current.
Figure 4B:
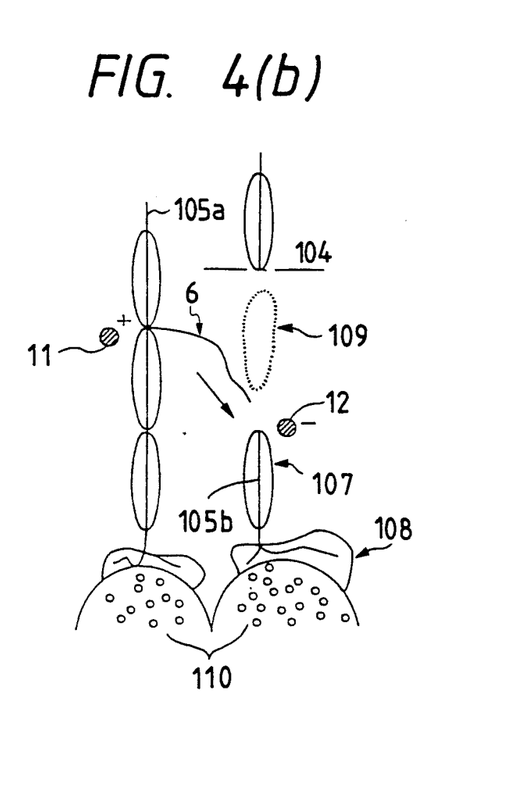

FIGS. 4(a) and 4(b) schematically show a mechanism of connecting nerve cells to each other with the aid of a micro-current. First, assume that as shown in FIG. 4(a) the right-hand nerve cell has been cut off at the position between the second and third Schwann cells 107d, 107e for some reason. In this case, a first electrode 11 is placed near the connecting point of the second and third Schwann cells 107a, 107b of the left-hand nerve cell, and a second electrode 12 is set near the connecting point of the first and second Schwann cells 107c, 107d of the right-hand nerve cell. Then, a micro-current is continuously supplied between the first and second electrodes 11, 12 whose potentials are set positive and negative, respectively. As a result, a lateral branch 6 germinates from an axis cylinder 105a of the left-hand nerve cell at the connecting point in the vicinity of the first electrode 11, and extends toward the second electrode 12 (FIG. 4 (b)). Finally, the lateral branch 6 reaches an axis cylinder 105b of the right-hand nerve cell, so that the two nerve cells are connected to each other. The facilitation of the germination and extension of the axis cylinder is considered due to drift of special substances such as growth factor proteins by the application of a micro-current.

Returning to FIG. 1, it is assumed that muscle fibers 110 and nerve cells are exposed from a living body 1 (e.g., a mouse) which is set at a predetermined position on a working table (not shown). An optical lens 21 and a CCD camera 22 are provided above the working table so as to observe the living body 1. An output (video signal) of the CCD camera 22 is sent to a TV monitor 23. The optical lens 21 and the CCD camera 22 are movably mounted on a frame 24 so as to observe a desired portion of the living body 1. The first and second electrodes 11 and 12 are stabbed into the nerve cells of the living body 1, and a body casing 10 holding the respective proximal ends of the first and second electrodes 11, 12 is attached to a manipulator 25. The manipulator 25 is fixed to the end of an arm 26 extending from the frame 24.

Further, a stimulating electrode 31 for electrically stimulating the nerve cells and a monitor electrode 32 for detecting a reaction to the stimulation are stabbed into the living body 1. The electrodes 31, 32 are connected to a pulse generator 33 and an oscilloscope 34. The pulse generator 33 generates a pulse voltage for stimulating the nerve cells of the living body 1 at predetermined time intervals. The oscilloscope 34 displays a waveform of the stimulation pulse voltage which is generated by the pulse generator 33 and applied to the living body 1 via the stimulating electrode 31 as well as a waveform of a reaction pulse detected by the monitor electrode 32, with the same time scale.

Figure 2A:
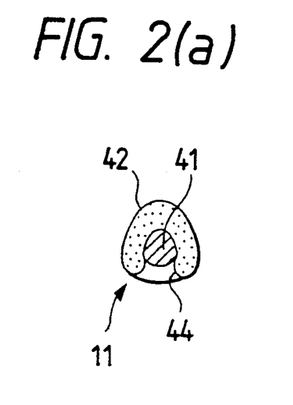
FIGS. 2(a)-2(c) are views showing the construction of electrodes to be used in the apparatus of FIG. 1.
Figure 2B:
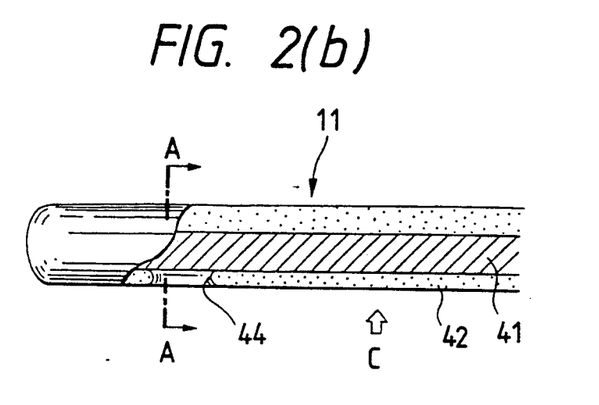
Figure 2C:
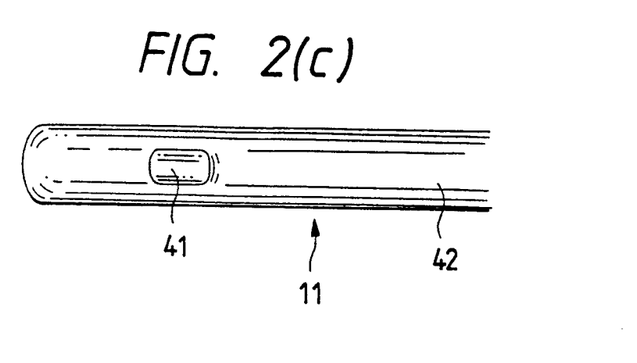

FIGS. 2(a)-2(c) show the detailed structure of the electrode 11 to be used in the apparatus of FIG. 1. FIG. 2(b) is a partially sectional side view, FIG. 2(a) a sectional view taken along line A—A in FIG. 2(b), and FIG. 2(c) is a view as viewed along arrow C in FIG. 2(b).

As shown in FIGS. 2(a)-2(c), the first electrode 11 has, in its center, a needle-like member 41 made of, e.g., platinum and covered with an insulating cover member 42. A typical diameter of the first electrode 11 is 0.1 mm. Part of the insulating cover member 42 is removed at a side position in the vicinity of the distal end so as to expose the needle-like member 41. The second electrode 12 has a similar structure to the first electrode 11. Although not shown in the figures, a needle-like member 41 of the second electrode 12 is also exposed at the position opposite to the exposed part of the first electrode 11. According to this structure, since a substantially pointed electrode is provided in which only the exposed surface of the needle-like member 41 actually works, a resultant electric field distribution can easily be controlled.

Figure 3A:
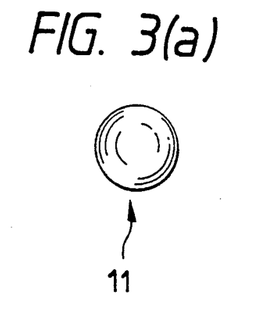
FIGS. 3(a) and 3(b) are views showing the construction of another example of electrodes to be used in the apparatus of FIG. 1.
Figure 3B:
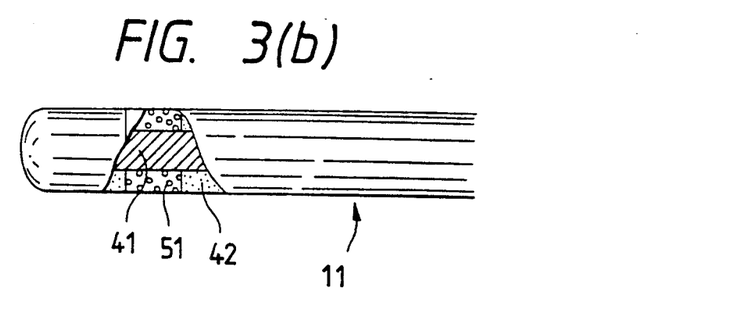

FIGS. 3(a) and 3(b) show another structure of the first electrode 11 to be used in the apparatus of FIG. 1. In this example, a needle-like member 41 is not exposed, but a porous member 51 is provided to make current conduction possible. The porous member 51 should be a material through which a medium such as physiological saline can permeate.

Next, a description will be made as to the procedure of connecting nerve cells to each other using the apparatus of FIG. 1. First, the living body 1 is fixed to the working table; the magnification, focal length, position on the frame 24, of the optical lens 21, etc. are adjusted; and a portion to be worked of the living body 1 is observed by the TV monitor 23. Then, the manipulator 25 is operated so as to stab the first and second electrodes 11, 12 into the tissue of the living body 1 at the appropriate positions. The stimulating electrode 31 and the monitor electrode 32 are also stabbed into the living body 1, more specifically, at the respective end portions of the two nerve cells to be connected. (In FIG. 4(a), the stimulating electrode 31 is stabbed into an upper Schwann cell of the left-hand nerve cell.) Next, a controller (not shown) operates to apply a DC voltage across the first and second electrodes 11, 12 so that a micro-current flows through the living body 1 between the electrodes 11, 12. A typical value of the strength of an electric field created by the DC voltage is several tens of millivolts/cm. While the micro-current is flowing, electric stimulation is applied from the pulse generator 33 to the living body 1 via the stimulating electrode 31 at predetermined time intervals, and the reaction is observed with the oscilloscope 34 via the monitor electrode 32. When the reaction to the stimulation appears, it is judged that the desired connection of the nerve cells has been completed, and the application of the DC voltage across the first and second electrodes 11, 12 is stopped. This completes the work of making a lateral branch germinate and extend from the axis cylinder of one of the nerve cells and connecting the lateral branch to the other cell. Typically, the DC voltage needs to be kept applied for 30 minutes to several hours.

Figure 5A:
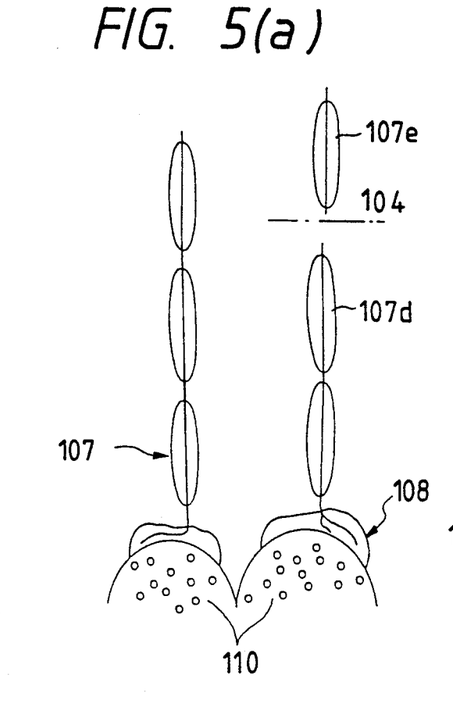
FIGS. 5(a)-5(c) are diagram schematically showing how Schwann cells are fused by a high voltage pulse current.
Figure 5B:
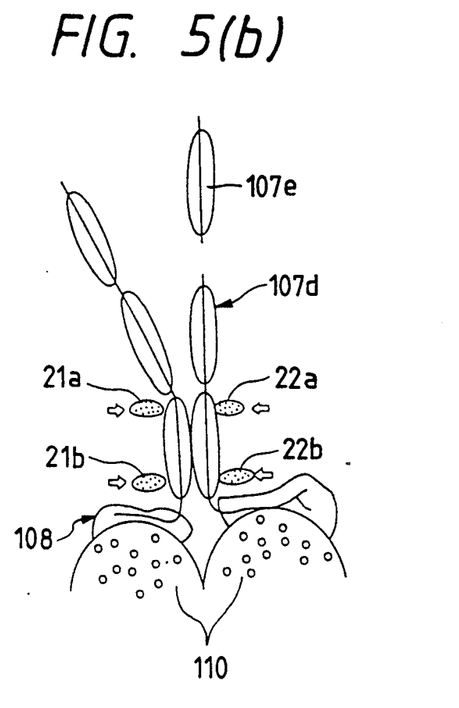
Figure 5C:
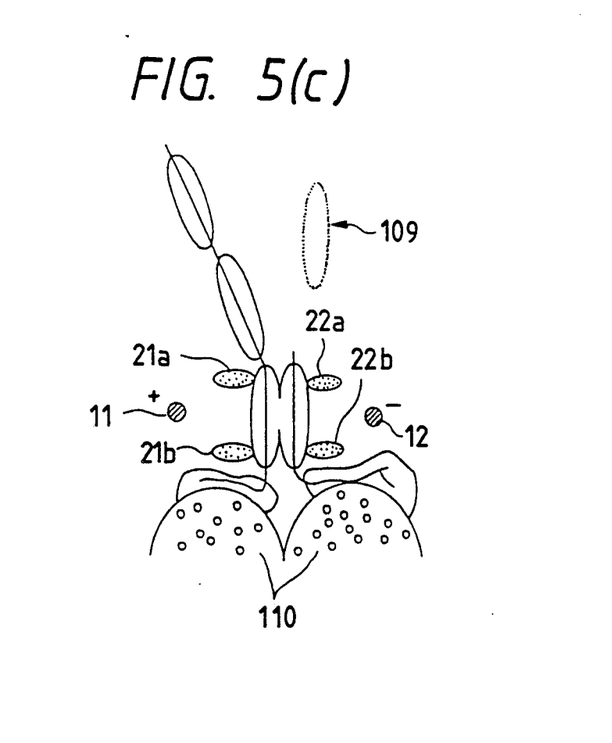

In addition to the case of connecting nerve cells using a micro-current as shown in FIGS. 4(a) and 4(b), the apparatus of FIG. 1 can also be used for the case of connecting nerve cells using a high voltage pulse current as shown in FIGS. 5(a)-5(c).

FIGS. 5(a)-5(c) schematically show a mechanism of connecting nerve cells using a high voltage pulse current. Assume that the right-hand nerve cell has been cut off between the second and third Schwann cells 107d, 107e for some reason as shown by line 104 in FIG. 5(a). In the technique under consideration, a jig such as tweezers is used to apply physical external force to the nerve cells so as to bundle them. That is, as shown in FIG. 5(b), the two Schwann cells of the two nerve cells are grasped by two pairs of grasping members 21a, 22a and 21b, 22b so as to contact with each other by their side surfaces, or to be placed sufficiently close to each other. With the two Schwann cells being grasped, a high voltage pulse is applied once or several times across the first electrode 11 disposed behind the grasping members 21a and 21b and the second electrode 12 disposed behind the grasping members 22a and 22b. Typical examples of the pulse width and the strength of an electric field created by the high voltage pulse are several tens to several hundreds of microseconds and several kilovolts/cm, respectively. As a result, the outer shells of the two Schwann cells are broken, and the two Schwann cells are fused as shown in FIG. 5(c). Further, it is a matter of course that the nerve cells must be left as they are for a predetermined time after the fusion because the connection of the axis cylinders, i.e., nerve cells, will not complete immediately after the fusion of the Schwann cells.

In the case of utilizing the fusion of Schwann cells, it is necessary that a high voltage pulse is applied while the cells are kept in contact with each other. Therefore, it is desirable that the set of electrodes 11, 12 be adapted as shown in FIGS. 6(a)-6(f).

Figure 6A:
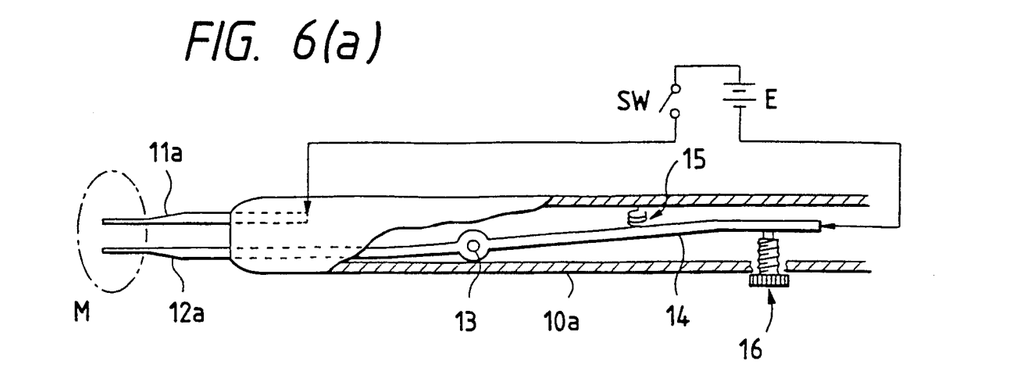
FIGS. 6(a)-6(f) are views showing the construction of an electrode set to be used in the apparatus of FIG. 1.

FIG. 6(a) is a partially sectional view showing the whole structure of an electrode set, and FIGS. 6(b)-6(f) are enlarged views showing main part M in FIG. 6(a). As shown in FIG. 6(a), a proximal portion of a first electrode 11a is fixed to a body casing 10a, and a second electrode 12a is arranged in parallel with the first electrode 11a. A proximal portion of the second electrode 12a extends into the body casing 10a so as to be rotatable about an axis 13 fixed to the body casing 10a. A lever portion 14 on the other side of the electrode portion is urged clockwise by a spring 15 whose one end is fixed to the inner surface of the body casing 10a. The position of the lever portion 14 is adjusted by a micrometer 16 threadedly engaged with a screw hole formed in the body casing 10a. Further, the first and second electrodes 11a, 12a are connected to a power source E, and the application of a high voltage pulse is controlled by a switch SW.

Figure 6B:
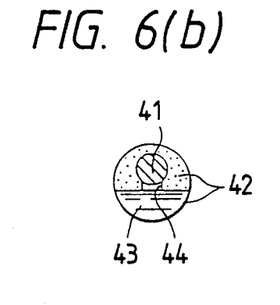
Figure 6C:
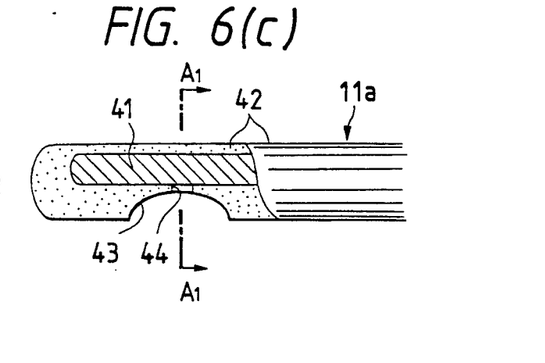
Figure 6D:
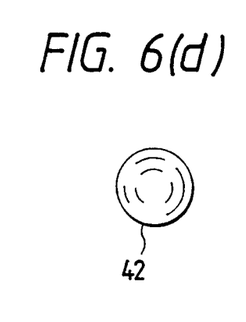
Figure 6E:
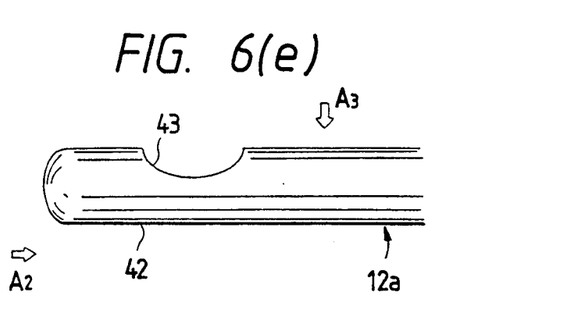
Figure 6F:
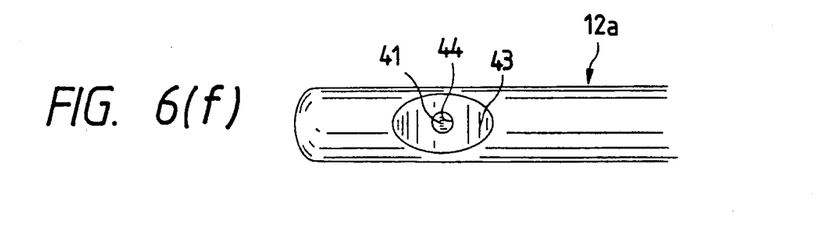

FIGS. 6(c) and 6(e) show the main parts of the first and second electrodes 11a, 12a, respectively, and indicate that the main parts are symmetrical and similar to each other. FIG. 6(c) is a partially sectional view, FIG. 6(b) is a sectional view taken along line $A_1-A_1$ in FIG. 6(c), and FIG. 6(d) is a view when the second electrode 12a is viewed along arrow $A_2$ in FIG. 6(e). Further, FIG. 6(f) is a view when the second electrode 12a is viewed along arrow $A_3$ in FIG. 6(e).

As illustrated in FIGS. 6(a)-6(f), each of the first and second electrodes 11a, 12a has, in its center, a needle-like member 41 made of, e.g., platinum and covered with an insulating cover member 42. Semicircular parts of the respective insulating cover members 42 are removed at their positions opposed to each other so as to form recesses 43. Further, a circular through hole 44 is formed at the center of each recess 43 to expose the needle-like member 41. It is noted that the surfaces of the recesses 43 constitute the two pairs of grasping members 21a, 22a and 21b, 22b shown in FIGS. 5(a) and 5(b). Instead of forming the through hole 44, the recess 43 may be formed in a porous material (see FIGS. 3(a) and 3(b)).

By using the electrode set having the foregoing structure, Schwann cells can be fused very effectively to connect nerve cells. The cell fusion procedure will be described with reference to FIGS. 1 and 7(a)-7(b).

Figure 7A:
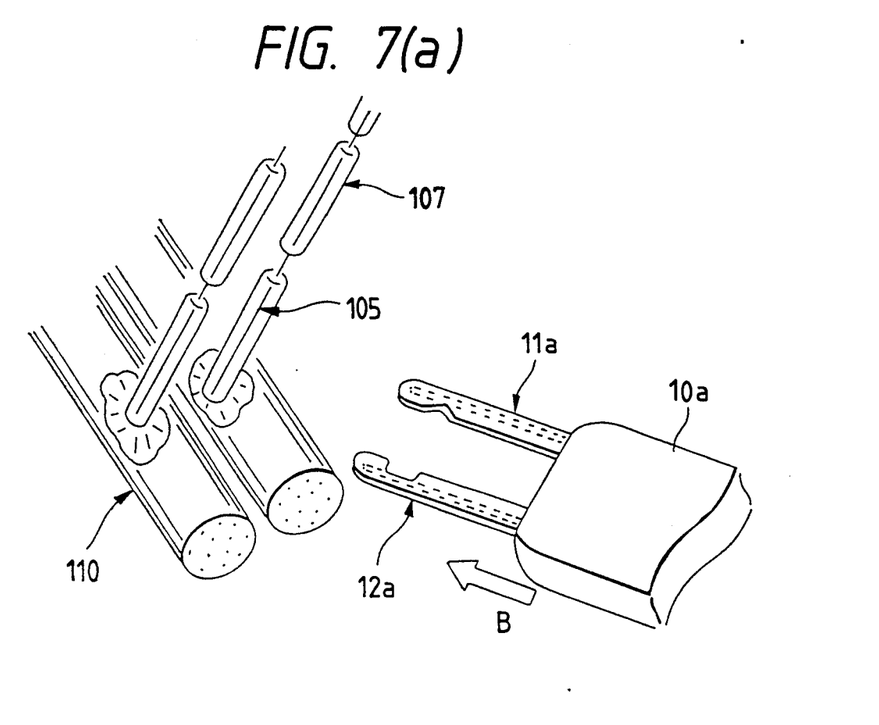
FIGS. 7(a) and 7(b) are views showing how the electrode set of FIGS. 6(a)-6(f) is used.
Figure 7B:
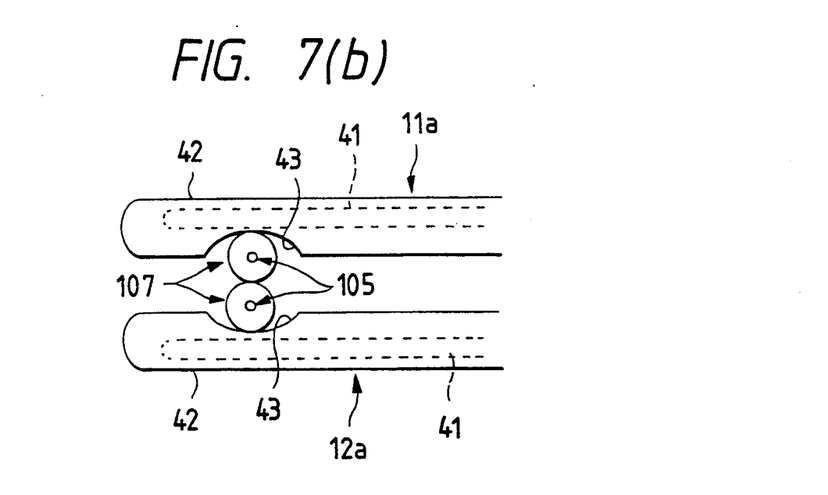

First, the manipulator 25 is operated while the living body 1 is observed with the TV monitor 23 (see FIG. 1) so that the body casing 10a is moved in the direction of arrow B in FIG. 7(a) with the interval between the first and second electrodes 11a and 12a kept large. Then, after Schwann cells 107 of two nerve cells to be connected are grasped, the micrometer 16 attached to the body casing 10a is rotated using the manipulator 25 so that the second electrode 12a approaches the first electrode 11a. This operation is continued until the positional relation of FIG. 7(b) is obtained, that is, until the two Schwann cells are bundled and contacted with each other between the recesses 43 of the first and second electrodes 11a, 12a. In this state, a pulse voltage is applied across the first and second electrodes 11a, 12a by operating the switch SW and, as a result, the Schwann cells are fused. The needle-like member 41 is hardly damaged because being shielded by the insulating cover member 42 it does not contact with the Schwann cell. Several hours after the fusion of the Schwann cells, the output pulse voltage of the pulse generator 33 is applied to the living body 1 via the stimulating electrode 31. The connection of the axis cylinders 105b can be confirmed through the observation of the reaction with the oscilloscope 34.

Although, in the above embodiments, the connection of nerve cells is confirmed by applying a pulse voltage across the stimulating electrode 31 and the monitor electrode 32, it may be confirmed by optically measuring, for instance, a shape variation of an excitement cell in a portion under operation or a variation of an absorption/emitted light intensity with external application of a monitoring dye.

As described above in detail, in the nerve connecting techniques according to the present invention, a pair of electrodes can be set near the nerve cells to be connected while the nerve cells re being observed with a TV monitor. Further, the connection of the nerve cells can be confirmed by applying electric stimulation to the object living body and monitoring its reaction appearing on an oscilloscope. Therefore, nerve cells can be connected easily in a positive manner.

What is claimed is:

1. An apparatus for connecting nerve cells of a living body, comprising:
   a pair of first electrodes, each first electrode arranged substantially in parallel with the other first electrode and separated from the other first electrode by a distance suitable for placing the pair of first electrodes near the nerve cells to be connected;
   manipulating means for adjusting a position of the pair of first electrodes;
   observing means for magnifying an image of a portion under operation of the living body, and for displaying the magnified image; and
   power source means for applying a voltage across the nerve cells to be connected via the pair of first electrodes.

2. The apparatus according to claim 1, further comprising:
   a pair of second electrodes, each second electrode to be stabbed into the portion of the living body under operation at opposite ends of the nerve cells to be connected;
   pulse generating means for applying a stimulation pulse voltage to the living body via the pair of second electrodes; and
   oscilloscope means for displaying a waveform of the stimulation pulse voltage and a waveform of a reaction pulse generated in the living body in response to the stimulation pulse voltage and detected via the pair of second electrodes.

3. The apparatus according to claim 1, wherein the voltage is a DC voltage which causes a micro-current to flow through the living body between the pair of electrodes.

4. The apparatus according to claim 1, wherein the voltage is a pulse voltage.

5. The apparatus according to claim 1, wherein the manipulating means further adjusts the distance between the pair of first electrodes.

6. An electrode unit for use in connecting tissues of a living body, comprising:
   a body casing; and
   a pair of electrodes attached to the body casing, each electrode arranged substantially in parallel with the other electrode and comprising:
   a needle-like electrode member;
   an insulating cover member for covering the needle-like electrode member; and conducting portion formed in the insulating cover member at a distal position of the electrode, the conducting portions of the pair of electrodes arranged so as to face each other enabling current conduction to the needle-like electrode members.

7. The electrode unit according to claim 6, wherein the conducting portion of the insulating cover member includes a through hole for exposing a part of the needle-like electrode member.

8. The electrode unit according to claim 6, wherein the conducting portion includes a porous material.

9. The electrode unit according to claim 6, further comprising a mechanism for adjusting a distance between the pair of electrodes.

10. The electrode unit according to claim 6, wherein a portion of the insulating cover member including the conducting portion is in a recess.

11. The electrode unit according to claim 6, wherein the tissues are nerve cells.

12. A method for connecting nerve cells of a living body, comprising the steps of:
    placing a first electrode near a first nerve cell, and a second electrode near a second nerve cell to be connected to the first nerve cell;
    applying a DC voltage across the first and second electrodes the first and second electrodes being the cathode and anode respectively, until a lateral branch germinates from an axis cylinder of the first nerve cell and extends toward the second nerve cell, and finally reaches an axis cylinder of the second nerve cell.

13. The method according to claim 12, further comprising:
    applying a stimulation pulse voltage to the living body at a predetermined interval while applying the DC voltage;
    detecting a reaction of the living body to the stimulation pulse voltage;
    stopping application of the DC voltage when connection of the first and second nerve cells is confirmed through detection of the reaction.

14. A method for connecting nerve cells of a living body, comprising the steps of:
    placing each electrode of a pair of electrodes on opposite sides of the nerve cells to be connected;
    grasping the nerve cells to be connected by the pair of electrodes so that the nerve cells are contacted with each other or placed closely;
    applying a pulse voltage across the pair of electrodes until the nerve cells fuse together.

15. The method according to claim 14, further comprising:
    applying a stimulation pulse voltage to the living body; and
    detecting a reaction of the living body to the stimulation pulse voltage to confirm connection of the nerve cells.

16. The method according to claim 14, wherein the pulse voltage is applied a plurality of times.

17. The method according to claim 14, wherein Schwann cells of the nerve cells are grasped by the pair of electrodes, and fused by application of the pulse voltage.

* * * * *